United States Patent [19]

Uchida et al.

[11] 4,247,628
[45] Jan. 27, 1981

[54] COLOR PHOTOGRAPHIC MATERIAL IMPROVED IN FADING PROPERTIES

[75] Inventors: Takashi Uchida; Shoji Kikuchi, both of Hachioji; Takashi Sasaki, Hino; Mikio Sato, Ebina, all of Japan

[73] Assignee: Konishiroku Photo Industry Co., Ltd., Nihonbashi-Muro, Japan

[21] Appl. No.: 109,273

[22] Filed: Jan. 3, 1980

Related U.S. Application Data

[63] Continuation of Ser. No. 883,942, Mar. 6, 1978, abandoned.

[30] Foreign Application Priority Data

Mar. 8, 1977 [JP] Japan .................................. 52/25064

[51] Int. Cl.$^3$ .......................... G03C 1/40; G03C 7/00
[52] U.S. Cl. .................................... 430/551; 430/372; 430/552
[58] Field of Search ....................... 430/551, 552, 372

[56] References Cited

U.S. PATENT DOCUMENTS

| 3,705,805 | 12/1972 | Nittel et al. | 430/512 |
| 3,841,877 | 10/1974 | Willems et al. | 430/382 |
| 4,009,038 | 2/1977 | Arai et al. | 430/551 |

FOREIGN PATENT DOCUMENTS 879144 10/1961 United Kingdom ..................... 430/372

Primary Examiner—J. Travis Brown
Attorney, Agent, or Firm—Haseltine, Lake & Waters

[57] ABSTRACT

The stability of a cyan dye image formed by phenol and naphthol couplers is improved with respect to "dark fading" by incorporating in the silver halide color photographic material in which the dye image is formed at least one 2-phenyl benzotriazole compound having in the 2'-position an —OR group wherein R is an organic residue.

2 Claims, No Drawings

COLOR PHOTOGRAPHIC MATERIAL IMPROVED IN FADING PROPERTIES

This is a Rule 60 Continuation of U.S. Patent Application Ser. No. 883,942, filed Mar. 6, 1978, now abandoned.

This invention relates to a silver halide color photographic material, in particular a silver halide color photographic material to produce stabilized dye image.

It is known to develop exposed silver halide particles with an aromatic primary amine compound and to react the resulting oxidation product of the amine with a coupler to form a dye image, thus giving a color image in a silver halide color photographic material. According to this process, yellow, magenta and cyan dye images are formed generally by using an acylacetamide or benzoylmethane coupler, a pyrazolone, cyanoacetyl or indazolone coupler and a phenol or naphthol coupler, respectively.

It is desirable that the color of a dye image thus formed does not change or fade, even after exposure to light or long-time storage in the dark, by the influence of moisture in the atmosphere where it is allowed to stand or where a chemical substance exists even in a slight amount or by heat.

A number of phenol or naphthol couplers which can be used to form a cyan dye image are known. It is also well known in general, however, that the cyan dye image formed by such couplers shows outstanding changing and fading in its color (referred to hereinafter as "dark fading") as compared with yellow or magenta dye image, particularly due to the moisture in the atmosphere when it is stored in the dark, or due to a very slight amount of chemical substance or heat. For improvements of the above dark fading of a cyan dye image, various proposals have been given. For example, as described in U.S. Pat. Nos. 2,579,436; 2,983,607; 3,095,302; 3,291,606; 3,201,243; 3,201,244; 3,473,929; 3,666,468 and 3,676,136 and Japanese Patent Publications No. 47-47245 and No. 48-18257, there is proposed a treatment of a color photograph in a stabilizing bath containing a hydantoin compound, carbohydrazide, sugar, amino acid derivative, etc. Further, in view of the fact that an unreacted coupler remaining after a developing treatment accelerates fading of dye image, U.S. Pat. No. 3,271,152 and British Pat. Nos. 843,940 and 849,065 disclose a method for elimination of such remaining coupler.

Although addition of a fading inhibiting agent to an emulsion layer is disclosed in Japanese Patent Publication No. 48-32728 in which a phosphorous acid ester is used as the fading inhibiting agent as well as in Japanese Patent Laid-Open Publication No. 50-151149 in which a 2-(2'-hydroxyphenyl)benzotriazole is employed, the following drawbacks are found therein: For example, when it is added to a treating bath, the surface of a color photograph after having been treated becomes sticky. When it is added to the emulsion, the background of the manufactured photosensitive material will be yellowed. Because a compound to be added is not satisfactorily soluble in a dispersion agent by which said compound is dispersed in the emulsion layer, the compound will be separated as crystal during the dispersing course or in the emulsion layer after the dispersion. According to another method, one additional treating bath is required. Further, the effect itself is not yet satisfactory.

The object of this invention is to provide a color photographic material which is simple and possesses particularly effective dye image preserving properties by adding thereto such compound as having good dark fading inhibiting effect to cyan dye image, high solubility in a high-boiling solvent, good dispersion stability and no adverse effect on other photographic additives and further causing no color developing inhibition to coupler.

After extensive researches, the inventors found that the above object of this invention can be achieved by letting the same layer contain at least one compound of the general formula (I) and a cyan dye image obtained from a phenol or naphthol cyan coupler represented by the general formula (I):

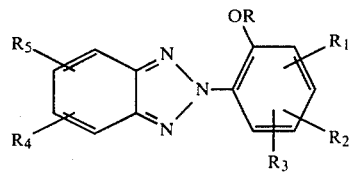

wherein R represents an alkyl, alkenyl, cycloalkyl, aryl, aralkyl, acyl, alkyl-sulfonyl or aryl sulfonyl group which includes the substituted and unsubstituted; an N-substituted carbamoyl or sulfamoyl group; an oxalyl, oxamoyl, oxycarbonyl or oxaacetyl group each having an alkyl, aryl, alkoxy or aryloxy group which includes the substituted and unsubstituted; $R_1$, $R_2$, $R_3$, $R_4$ and $R_5$ each represent hydrogen, halogen, an alkyl, alkenyl, aryl, aralkyl, alkoxy, aryloxy, acyloxy, alkylthio, arylthio, monoalkylamino, dialkylamino, acylamino, sulfonamido, or nitro group which includes the substituted or unsubstituted, the residue of sulfonic acid, its ester or its salt, the residue of carboxylic acid, its ester or its salt, or a heterocyclic group; $R_4$ and $R_5$ may cooperatively form a 5- or 6-membered carbocyclic ring. Among the compounds of the general formula (I), a compound of the general formula (II)

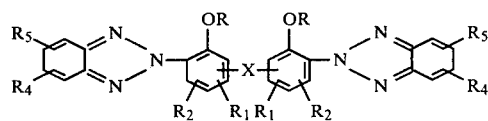

or the general formula (III)

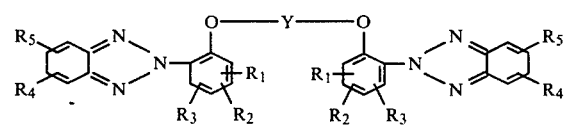

is included as a useful compound in the present invention.

In the above formulas (II) and (III), $R_1$, $R_2$, $R_3$, $R_4$ and $R_5$ are individually as defined in the formula (I) and X and Y each represent a divalent organic radical. For example, X represents an alkylene, alkylene dioxy, alkylene diamine, alkylene dicarbonyl or alkylene diamide chain which includes the substituted or unsubstituted, or such the chain having, in the midway of the chain, an arylene group, a two equivalent heterocyclic group or a two equivalent hetero atom; Y represents an alkylene chain which includes the substituted or unsubstituted or such the chain having, in the midway of the chain, an arylene group, a two equivalent heterocyclic group or a two equivalent hetero atom; or a bonding group having at both ends of each of the above chains carbonyl, sulfonyl, carbamoyl or sulfamoyl groups.

In the general formulas (I) and (II), R is preferably an alkyl, acyl, or alkyl- or aryl-sulfonyl, and acyl group is particularly preferable. In the general formula (III), Y is preferably a bonding group, both ends of which are carbonyl groups. These compounds are represented by the following general formulas (IV), (V) and (VI):

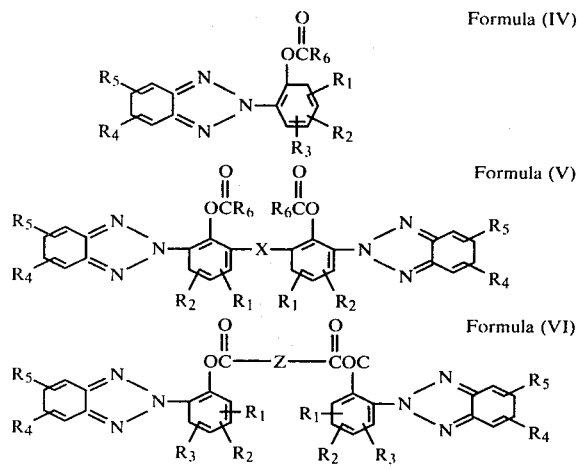

In the above formulas, $R_1$, $R_2$, $R_3$, $R_4$ and $R_5$ are individually as defined in the general formula (I), X is as defined in the general formula (II), $R_6$ represents a straight or branched alkyl, aryl, aralkyl or heterocyclic group and Z represents an alkylene chain, an arylene group or an alkylene chain having, in the midway, an arylene group, a two equivalent heterocyclic group or a two equivalent hetero atom.

Each of the compounds of the above formulas can be prepared from 2-(2'-hydroxyphenyl)benzotriazole compound by a primary and general synthetic process. Said 2-(2'-hydroxyphenyl)benzotriazole compound used as the starting material is now widely used in an organic material as UV absorber and a number of them are easily available as commercial products. They are easily synthesized by the processes disclosed in British Pat. No. 879,144; U.S. Pat. Nos. 3,042,669; 3,794,493 and 3,936,305; Japanese Patent Publication No. 36-10466 and No. 50-25337. Further, a number of such compounds are known from U.S. Pat. Nos. 3,004,896; 3,159,646; 3,253,921; 3,272,891; 3,282,886; 3,533,794; 3,692,525; 3,705,805; 3,738,837 and 3,754,919 and Japanese Patent Laid-Open Publication No. 50-151,149. Thus, any of 2-(2'-hydroxyphenyl)benzotriazole compounds can be used in the present invention as the starting material.

Typical examples of the compounds according to this invention will be given below but compounds usable in this invention should not be limited to these compounds.

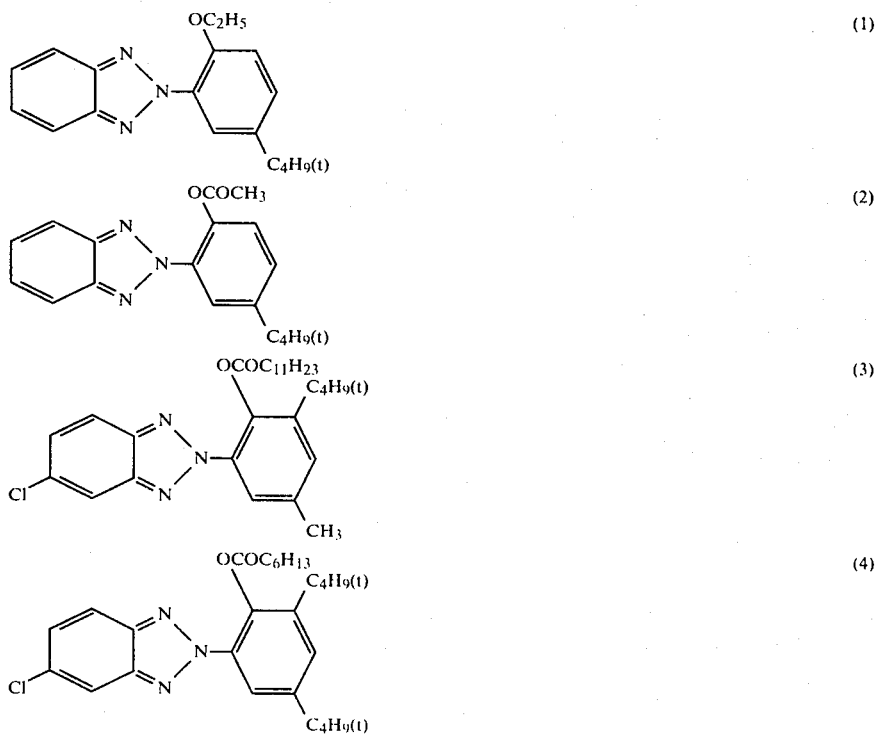

-continued
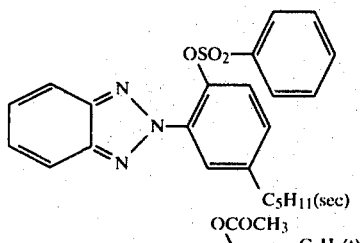 (5)
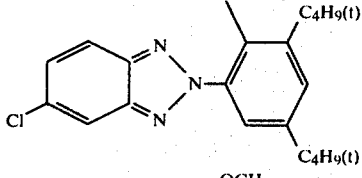 (6)
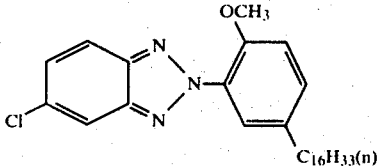 (7)
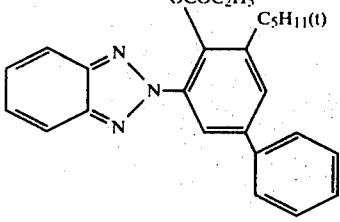 (8)
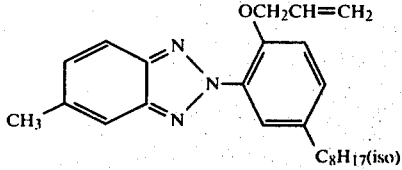 (9)
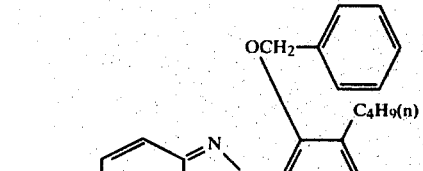 (10)
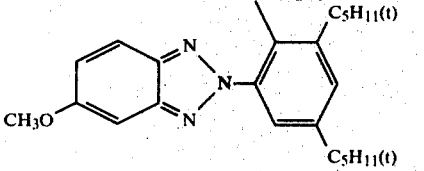 (11)
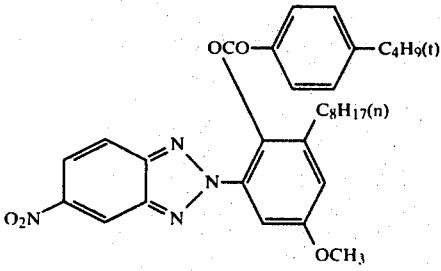 (12)

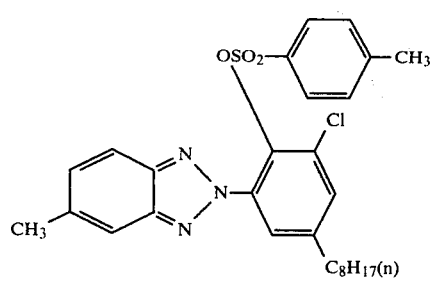
(13)
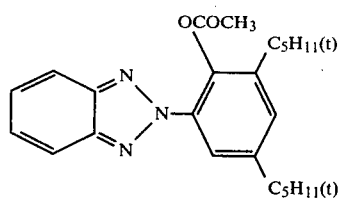
(14)
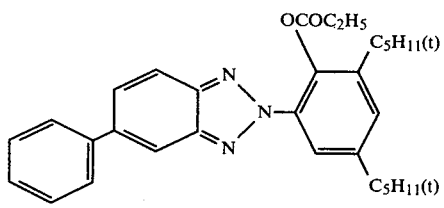
(15)
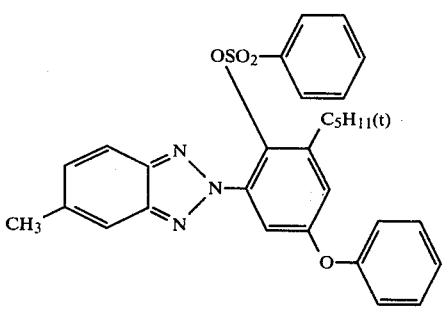
(16)
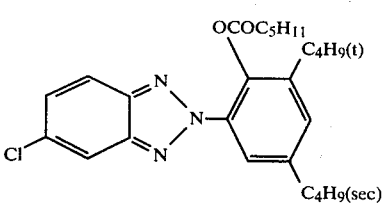
(17)
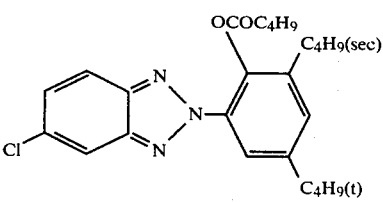
(18)
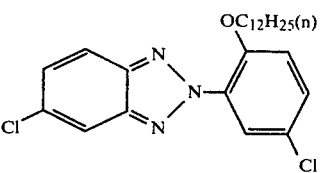
(19)

-continued
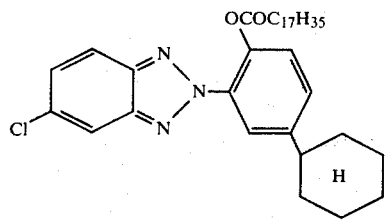 (20)
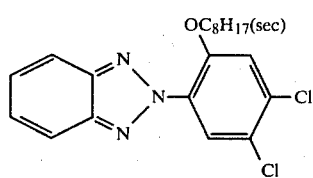 (21)
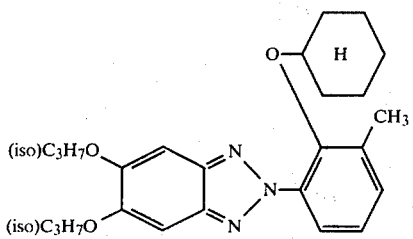 (22)
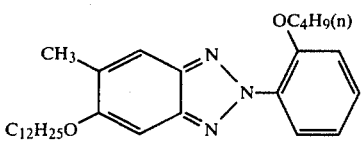 (23)
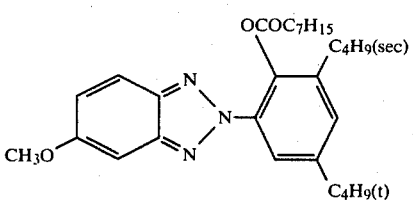 (24)
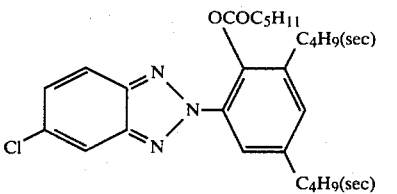 (25)
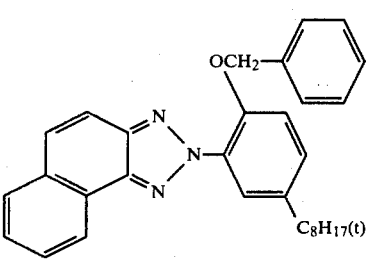 (26)
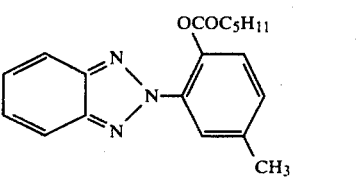 (27)

-continued
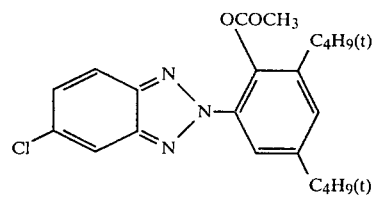 (28)
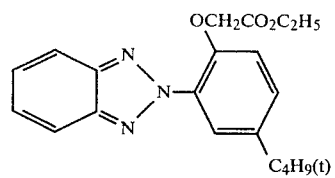 (29)
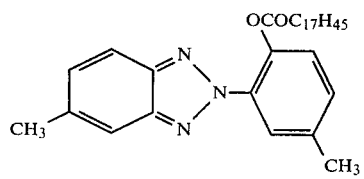 (30)
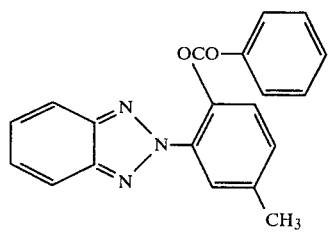 (31)
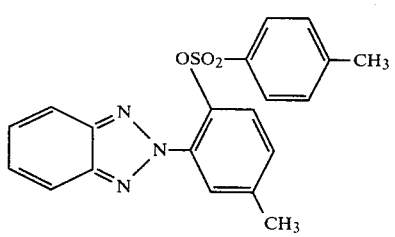 (32)
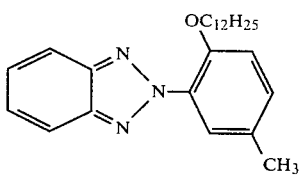 (33)
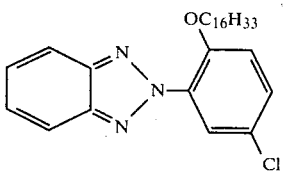 (34)
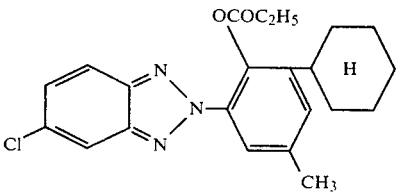 (35)

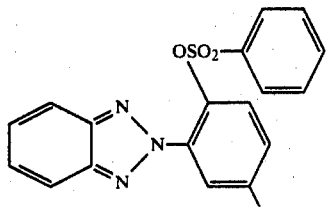
(36)
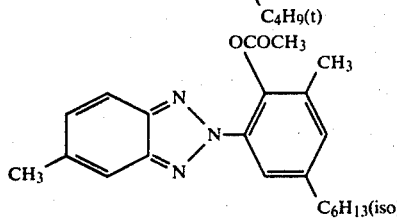
(37)
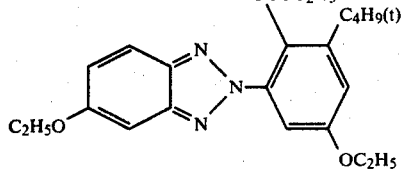
(38)
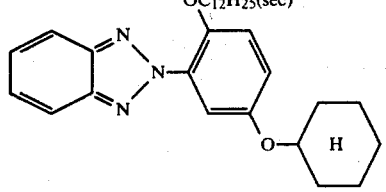
(39)
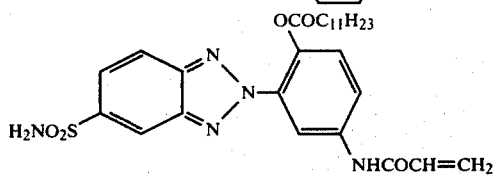
(40)
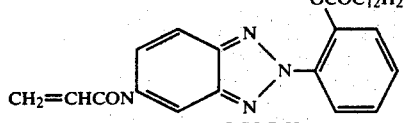
(41)
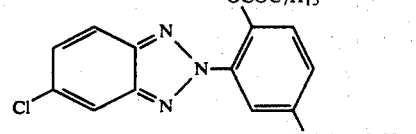
(42)
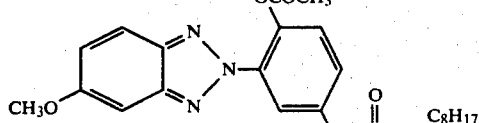
(43)
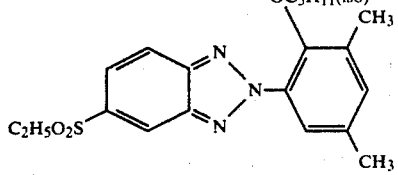
(44)

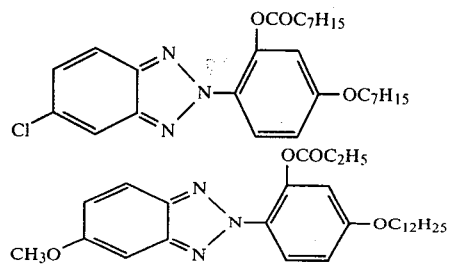

(45)

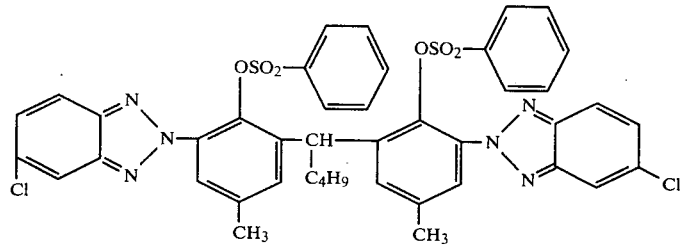

(46)

(47)

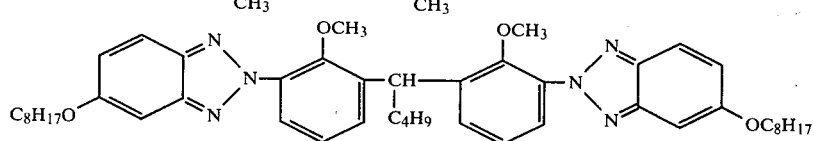

(48)

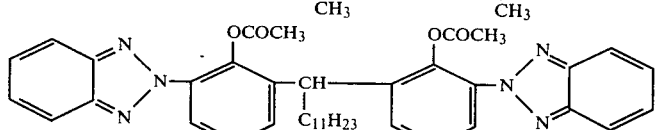

(49)

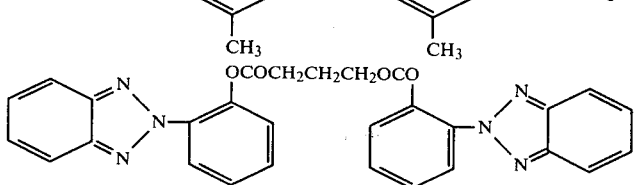

(50)

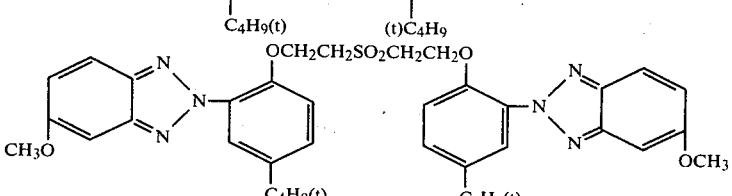

(51)

(52)

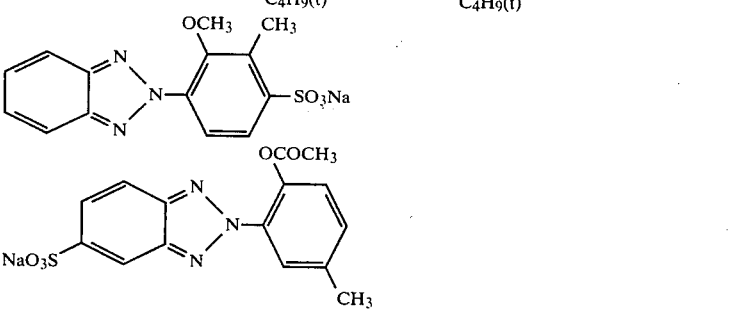

(53)

A part of the compounds of this invention are already known from the disclosures of British Pat. No. 879,144 and Japanese Pat. Publication No. 36-10466 and the other compounds can be synthesized quite similarly in a usual manner. The present invention is not related to a process for the synthesis. Such synthesis is quite conventional and the synthesis of a part of the compounds is already exemplified in many literatures but some syntheses will be exemplified below for convenience.

SYNTHESIS EXAMPLE 1 (Compound 28)

71.5 g of 2-(2'-hydroxy-3',5'-di-tert.butyl-phenyl)-5-chloro-benzotriazole and 20 ml of acetic anhydride are mixed and few drops of concentrated sulfuric acid are added thereto. The mixture is heated on a water bath for 30 minutes. After completion of the reaction, the resulting acetic acid and excess acetic anhydride are distilled off under reduced pressure and water is added to the residue to give white crystal. Recrystallization from methanol yields 67.6 g of white crystal.

The above product was identified by measurements of nuclear magnetic resonance spectrum (NMR), infrared spectrum (IR) and ultraviolet spectrum (UV) and elemental analysis.

m.p. 134°–135° C.

UV $\lambda_{max}$, 310 mμ

Analysis $C_{22}H_{26}ClN_3O_2$ (MW 399.5); Calcd.: C 66.08, H 5.51, N 10.51, Cl 8.89; Found: C 66.14, H 5.66, N 10.49, Cl 8.72

SYNTHESIS EXAMPLE 2 (COMPOUND 1)

54 g of 2-(2'-hydroxy-5'-tert.butyl-phenyl)-benzotriazole and 26.2 g of ethyl bromide are dissolved in 400 ml of acetone and 30.4 g of anhydrous potassium carbonate are added thereto. The solution is slowly warmed on a water bath with stirring and the reaction is effected for 4 hours by heating under reflux.

After completion of the reaction, the inorganic material is filtered off and acetone is removed by distillation to give a crystal, which is recrystallized from ligroin to afford white crystal. Yield 39.5 g.

The product was identified by measurements of NMR, IR and UV spectrum and elemental analysis.

m.p. 159°–160° C.

$\lambda_{max}$ 286 mμ

Analysis: $C_{18}H_{21}N_3O$ (MW 295); Cald.: C 73.19, H 7.17, N 14.23; Found: C 73.42, H 7.30, N 14.38;

SYNTHESIS EXAMPLE 3 (COMPOUND 36)

27 g of 2-(2'-hydroxy-5'-tert.butyl-phenyl)-benzotriazole are dissolved in 60 ml of pyridine and 23 g of benzenesulfonium chloride are added thereto. The mixture is reacted with stirring at a room temperature for 3 hours and then poured into a mixture comprising 80 ml of concentrated hydrochloric acid, 100 ml of water and 200 ml of methanol with stirring thoroughly to give a white crystal. This crystal is recrystallized from methanol to yield 31.5 g of the end product. The product was identified by measurements of NMR, IR and UV spectra and elemental analysis.

m.p. 125° C.

$\lambda_{max}$ 300 mμ

Analysis: $C_{22}H_{21}N_3O_3S$ (MW 407); Calcd.: C 64.86, H 5.17, N 10.31, S 7.87; Found: C 64.99, H 5.29, N 10.35, S 7.62

The cyan dye image forming coupler as used in this invention is either a 4 equivalent-type of phenol and naphthol coupler or a 2 equivalent-type phenol or naphthol coupler having a split-off group. These couplers are already described, for example, in U.S. Pat. Nos. 2,423,730; 2,474,293; 2,801,171; 2,895,826; 3,476,563; 3,737,326; 3,758,308 and 3,839,044, Japanese Patent Laid-Open Publication No. 47-37425; No. 50-10135; No. 50-25228; No. 50-112038; No. 50-117422 and No. 50-130441 as well as Research Disclosure (1976) 148, 53, etc. Typical cyan couplers will be exemplified below.

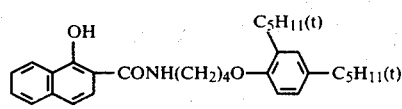
C-1

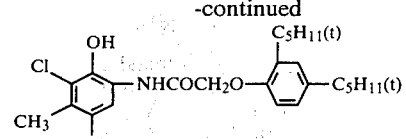
C-2

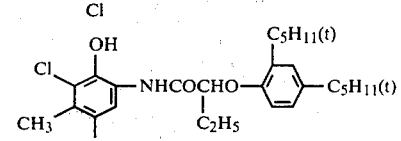
C-3

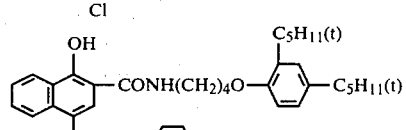
C-4

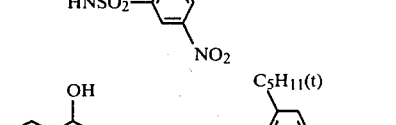
C-5

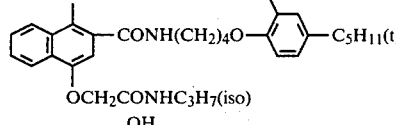
C-6

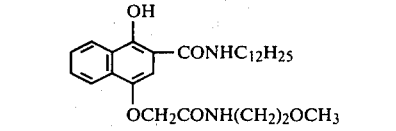
C-7

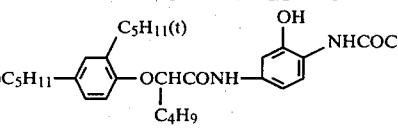
C-8

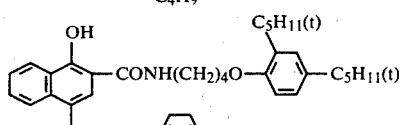
C-9

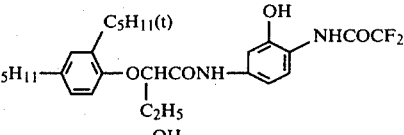
C-10

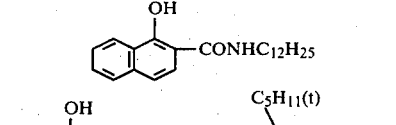
C-11

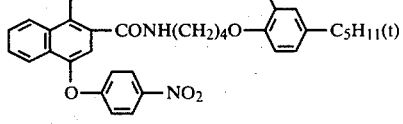
C-12

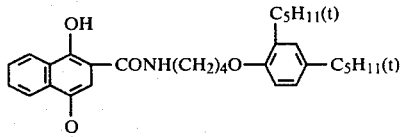
C-13

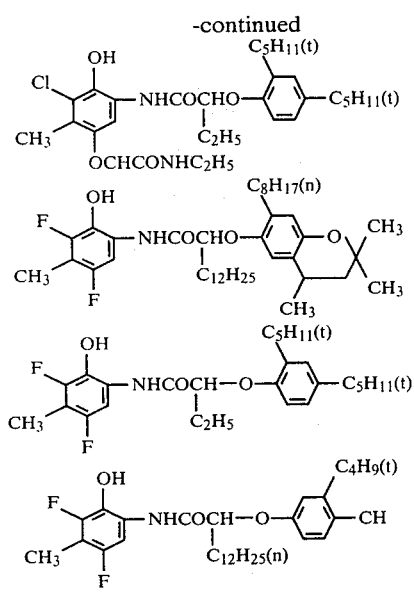

The cyan coupler which can be used in this invention is not limited to any one of the above-mentioned coupler but can be selected widely and further two or more can be used in combination.

When the coupler is incorporated into a silver halide color photographic material, it is used in general in an amount of 5-50 mole %, preferably 10-30 mole % of the silver halide and when the coupler is incorporated into a developing solution, it is used in general in an amount of 0.5-3.0 g/l, preferably 1.0-2.0 g/l.

The compounds of general formula (I) according to the present invention are generally soluble in an oil and can be used by being dissolved according to the process described in U.S. Pat. Nos. 2,322,027; 2,801,170 and 2,304,940 together with couplers in a high-boiling solvent, for example, an organic acid amide, carbamate, an ester, ketone, urea derivatives, hydrocarbon, etc., in particular di-n-butyl phthalate, tricresyl phosphate, diisooctyl azelate, di-n-butyl sebacate, tri-n-hexyl phosphate, N,N-di-ethyl-caprylamide butyl, n-pentadecyl phenyl ether, decalin, fluorine paraffin, or a low-boiling solvent, for example, ethyl acetate, butyl acetate, butyl propionate, cyclohexanol, cyclohexane, tetrahydrofuran used alone or in combination, mixed with an aqueous solution containing a hydrophilic binder such as gelatin containing an anion surfactant, for example, an alkylbenzenesulfonic acid or alkylnaphthalenesulfonic acid and/or a nonionic surfactant, for example, sorbitan sesquioleicacid ester, sorbitan monolauric acid ester, emulsified and dispersed by means of a high speed rotary mixer, colloid mill or supersonic dispersion apparatus and then added to a silver halide emulsion. The resulting coupler-containing silver halide emulsion is coated on a suitable support, for example, a glass plate, synthetic resin plate, various film bases, baryta paper, polyethylene laminated paper, etc. and then dried to give a silver halide color photographic material.

When a coupler used is diffusible, such coupler may be added to a color developing solution while the compound of general formula (I) according to this invention may be emulsified and dispersed alone and then added to a silver halide emulsion.

The compounds according to this invention exhibit satisfactory effect even when the compounds are included in silver halide color photographic material by treating the color photographic material which has been subjected to developing with a treating solution containing said compounds according to the present invention. There is no particular limitation in an amount of the compounds according to the present invention to be added, because they are quite colorless and consequently there is caused no adverse effect such as coloring, color-contamination, etc. on the resulting color photographic material due to such compounds. However, in a coupler containing silver halide color photographic material, 5-300% by weight of the present compound based on the coupler used is preferable and 10-100% by weight is particularly preferable.

In a coupler-free silver halide color photographic material, 10-100 g, particularly 15-60 g of the present compound of general formula (I) per mol of a silver halide are preferable.

Application of the present compounds of formula (I) to a photographic material is described in Japanese Patent Publication No. 36-10466, suggesting slightly that a part of the present compounds exhibit the use as a photographic material. Said Japanese Patent Publication No. 36-10466, however, claims apparently the characteristic use of a part of the present compounds as a UV absorber in an organic material. Further, considering the technical level of color photograph at the time when the above Japanese Patent Publication No. 36-10466 was filed, the invention described in said Japanese Patent Publication should distinctly be differentiated from the technique of the present invention to prepare a photographic material which is surprisingly improved in the dark fading of cyan dye image due to wetness and heat by including, according to the characteristic feature of the present invention, one or more of the present compounds in the same layer as the cyan dye image which is formed from phenol and/or naphthol cyan coupler.

On the other hand, an invention which comprises an idea similar to that of the present invention is disclosed in Japanese Patent Laid-Open-to-Public No. 50-151149 and the use of 2-(2'-hydroxyphenyl)benzotriazole is proposed therein. The particular excellence of the present compounds over said prior proposal resides primarily in their high effectiveness. This is surprising to the inventors themselves and such effect will be made apparent from Examples given later herein. What is particularly mentioned subsequently is high solubility of the present compounds in a solvent. In view of the fact that as described in U.S. Pat. No. 3,705,805 and Japanese Patent Publication No. 48-5496, a number of 2-(2'-hydroxyphenyl)benzotriazoles are less soluble and unstable in the dispersion, the advantage of the present compounds is quite particular.

Further advantage of the present compounds resides in the fact that all the maximum absorption points ($\lambda_{max}$) of the present compounds at the longest wavelength present at near 300 m$\mu$ and the compounds themselves are quite colorless. Therefore, even when the present compounds are added to a photographic material in a large amount, no coloration of the photographic material due to the added present compounds occur.

There is often used a fluorescent brightening agent in a photographic material in order to have white background appear clear. However, use of a large amount of such compound as having too strong UV absorptive power in a photographic material results in after all inhibition of the fluorescent brightening effect to be provided. In contrast to 2-(2'-hydroxyphenyl)benzotriazoles which possess strong UV absorptive effect, the compounds according to this invention possess almost no substantial UV absorptive effect and consequently no inhibition of fluorescent brightening effect occur.

The emulsion layer containing a present compound of the general formula (I) or (II) and a cyan coupler is able to contain further a developing inhibitor releasing type substance (so-called DIR substance) or a developing inhibitor releasing type coupler (DIR coupler). These substances may be used alone or in combination of two or more of them. Typical developing inhibitor releasing type couplers include those described in British Patent 953,454, U.S. Pat. Nos. 3,148,062; 3,227,554; 3,701,783 and 3,733,201 and West German Pat. No. 1,800,420. Typical developing inhibitor releasing type substances include those described in U.S. Pat. Nos. 3,632,345 and 3,928,041, Japanese Patent Laid-Open-to-Public No. 49-77635; No. 49-104630; No. 50-36125; No. 50-15273 and No. 51-6724.

The silver halide emulsion used in the silver halide color photographic material according to this invention is in general a dispersion of silver halide particles in hydrophilic colloid and as the silver halide, silver chloride, silver bromide, silver chlorobromide, silver iodobromide and silver chloroiodobromide as well as the mixture thereof can be used. Such silver halide may be prepared by various processes such as an ammonia method, a neutral method, a so-called conversion method and a simultaneous mixing process. As the hydrophilic colloid in which the silver halide is dispersed, there are used generally gelatin and a modified gelatin such as phthalated gelatin and malonated gelatin. In place of a part or all of said gelatin and modified gelatin, albumin, agar, gum arabic, alginic acid, casein, partially hydrolysed cellulose derivatives, partially hydrolyzed polyvinyl acetate, polyacrylamide and its imidation product, polyvinyl pyrrolidone and copolymers of these vinyl compounds can also be used.

Further, the silver halide emulsion may be used in combination with a hydroquinone derivative which is an antioxidant known for a long time, for example a compound described in U.S. Pat. Nos. 3,236,893; 3,062,884; 2,816,028; 2,735,765; 2,732,300; 2,728,659; 2,722,556; 2,710,801; 2,704,713; 2,701,197; 2,675,314; 2,418,613; 2,403,721; 2,384,658; 2,360,290 and 2,336,327, British Pat. Nos. 557,750 and 557,802, German Patent Laid-Open-to-Public No. 2,149,789, Japanese Patent Laid-Open-to-Public No. 46-2128, Journal of the Organic Chemistry, 72, 772–774, etc. Among such hydroquinone derivatives, a derivative in which a substituent on an aromatic nucleus is an alkyl group which includes the substituted or unsubstituted, is particularly preferable. As particularly preferable compounds, 2,5-di-octylhydroquinone, 2,5-di-tert.amyl-hydroquinone and 2,5-di-tert.butyl-hydroquinone are mentioned.

Further, it is also convenient to use the silver halide emulsion in combination with a UV-absorber. As the UV-absorber, there may be used, for example, one described in U.S. Pat. Nos. 2,739,888; 3,004,896; 3,253,921; 3,533,794; 3,692,525; 3,694,211; 3,698,907; 3,705,805; 3,738,837; 3,754,919; 3,052,636; 3,707,375 and 3,936,305, British Pat. No. 1,321,355, Belgian Pat. No. 833,511, etc.

The silver halide emulsion may optically be sensitized by means of various sensitizing dyes in order to impart it light sensitivity at the desired lightsensitive wavelength region. Preferably, a cyanine dye, merocyanine dye or composite cyanine dye as described, for example, in U.S. Pat. Nos. 1,939,201; 2,072,908; 2,739,149; 294,763; 2,213,995; 2,493,748 and 2,519,001, West German Pat. No. 929,080 and British Pat. No. 505,979 can be used as the sensitizing dye, alone or in combination with two or more of them. Further, if necessary, there may be added to the silver halide emulsion various photographic additives such as a chemical sensitizer such as a thioether compound, a quaternary ammonium salt compound or a polyalkyleneoxide compound; a stabilizer such as triazoles, imidazoles, azaindense, benzothiazoliums, zinc compounds, cadmium compounds and mercaptans; a hardening agent such as a chromium salt, a zirconium salt, a mucochloric acid, an aldehyde- or triazine-polyepoxy compound as described in Japanese Patent Publication No. 34-7133 and No. 46-1872, U.S. Pat. Nos. 682,641; 3,736,320; 3,362,827 and 3,323,287, British Pat. Nos. 686,440 and 1,332,647; triethylene-phosphamide- or ethyleneimide-series hardening agent; a dihydroxyalkane plasticizer such as glycerine and 1,5-pentanediol; a fluorescent brightening agent; an antistatic agent; a coating aid, etc., alone or in combination with two or more of them. The resulting silver halide emulsion is mixed with a dispersion in which a compound of the general formula (I), (II) or (III) according to the present invention is dispersed and coated, if necessary, through a sub layer, an inter layer or a protective layer on a support of a synthetic resin film such as cellulose acetate, cellulose nitrate, polycarbonate, polyethylene terephthalate or polystyrene, baryta paper, polyethylene coating paper or glass plate to obtain a silver halide color photographic material.

A compound of the general formula (I) of the present invention may be contained even in a layer other than that forming a cyan dye image, for example, in filter layer, protective layer, back layer or other emulsion layer, without causing any adverse effect.

When the process of this invention is applied to the manufacture of a multi layer color photographic material, there may be widely used a yellow dye image forming coupler of benzoylacetanilide type, pivaloyl acetanilide type or 2 equivalents type wherein the carbon atom on which coupling occurs is substituted with a substituent capable of being split off during the coupling reaction (so-called a split-off group) as the yellow dye image forming coupler. These couplers are described, for example, in U.S. Pat. Nos. 2,875,057; 3,265,506; 3,664,841; 3,408,194; 3,447,928; 3,277,155 and 3,415,652, Japanese Patent Publication No. 49-13576, Japanese Patent Laid-Open-to-Public No. 48-29432; No. 48-66834; No. 49-10736; No. 49-122335; No. 50-28834 and No. 50-132926. As the magenta dye image forming coupler, there may be widely used a 5-pyrazolone-, pyrazolotriazole-, pyrazoline-benzimidazole-, indazolone- or split-off group bearing 2 equivalents type magenta dye image forming coupler. Such coupler is described, for example, in U.S. Pat. Nos. 2,600,788; 3,062,653; 3,127,269, 3,311,476; 3,419,391; 3,519,429; 3,558,318; 3,684,514 and 3,888,680, Japanese Patent Laid-Open-to-Public No. 49-29639; No. 49-111631; No. 49-129538 and No. 50-13041, Japanese Patent Application No. 50-24690; No. 50-134470 and No. 50-156327, British Pat. No. 1,247,493, Belgian Pat. No. 792,525, U.S. Pat. No. 3,061,432, West German Pat. No. 2,156,111, Japanese Patent Publication No. 46-60479 and Belgian Pat. No. 769,116.

The color photographic material according to this invention can be applied to every type of the coupler containing, silver halide color photographic material (Agfa type) and the silver halide color photographic material containing coupler in developing agent (Kodak type), such as color negative film, color positive film, color reversal film, color paper, etc. In particular, application to the coupler containing, silver halide color photographic material (Agfa type) is convenient and, after exposure, color developing is conveniently effected according to the color developing method. Further, the color photographic material according to this invention may be applied to such silver halide color photographic material in that a coupler and a principal color developing agent are included in the same layer, while being protected so that no contact therebetween may occur during said photographic material is unexposed, but after the exposure, they can contact to each other, or to such coupler-containing silver halide photographic material, in which a principal color developing agent is included in a coupler-free layer, and said principal color developing agent is moved when an alkaline treating solution is permeated to that said principal color developing agent may be brought into contact with the coupler. Further, in a silver halide color photographic material for use in the difusion transfer process, the compounds of formula (I) according to the present invention can be used by adding them to a light-sensitive element and/or image receiving element of the light-sensitive material. It is particularly convenient to add the present compounds to the image receiving element. In the reversal method, developing is effected by use of a developing solution for black and white negative and then exposure to white light is applied, or a treatment is effected in a bath containing fogging agent such as a boron compound and then color developing is effected by use of an alkali developing solution which contains a principal color developing agent. In this case, the fogging agent can be added to said alkali developing solution which contains the principal color developing agent without causing any adverse effect. After the color developing, bleaching is generally effected with a bleaching solution containing as the oxidizing agent ferricyanide or the ferric salt of aminopolycarboxylic acid and then fixing is effected with a fixing solution containing a solvent for silver salts, such as a thiosulfate, etc. to remove the silver image and the remaining silver halide, leaving thereby a dye image only. It is also possible to effect the bleaching and fixing by using a monobath bleach-fixing solution which contains both the oxidizing agent such as the ferric salt of an aminopolycarboxylic acid and a solvent for silver salts such as a thiosulfate, in place of using the bleaching solution and the fixing solution. Further, in combination with the color developing, bleaching, fixing, or bleaching and fixing, such treatment as pre-hardening, neutralization, washing with water, stopping, stabilization, etc. can be effected. In particular, the treating steps according to which the silver halide color photographic material of the present invention can conveniently be developed comprise, for example, color developing, optional washing with water, bleach-fixing, washing with water, optional stabilization, and drying. This course of steps may be carried out at a high temperature, e.g. above 30° C. and in a very short period of time. Typical treating steps and typical composition of each of the treating solutions used are shown below. Treatment Steps (30° C.):

|  | Treatment Time |
|---|---|
| Color developing | 3.5 min. |
| Bleaching and fixing | 1.5 min. |
| Washing with water | 2 min. |
| Stabilization | 1 min. |
| Drying | |
| Composition of Color Developing Solution: | |
| Benzyl alcohol | 5.0 ml |
| Sodium hexametaphosphoric acid | 2.5 g |
| Anhydrous sesium sulfite | 1.9 g |
| Sodium bromide | 1.4 g |
| Potassium bromide | 0.5 g |
| Borax ($Na_2B_4C_7 \cdot 10H_2O$) | 39.1 g |
| N-ethyl-N-β-methanesulfonamidoethyl-4-amine-aniline sulfate | 5.0 g |
| Water to make up | 1 l. |
| pH being adjusted to 10.30 with sodium hydroxide. | |
| Composition of Bleach-Fixing Solution: | |
| Ethylenediaminetetraacetic acid iron ammonium | 61.0 g |
| Ethylenediaminetetraacetic acid 2 ammonium | 5.0 g |
| Ammonium thiosulfate | 124.5 g |
| Sodium metabisulfite | 13.3 g |
| Anhydrous sodium sulfite | 2.7 g |
| Water to make up | 1 l. |
| pH being adjusted to 6.5 with aqueous ammonia. | |
| Composition of Stabilizing Solution: | |
| Glacial acetic acid | 20 ml |

800 ml of water is added and pH is adjusted to 3.5-4.0 with sodium acetate and thereafter water is added to make up 1 l.

Particularly useful principal color developing solution for use in the color developing of the silver halide color photographic material of this invention comprises a primary phenylenediamine, aminophenol and derivatives thereof and the following compounds may be included as typical exemplification:

Salts of N,N-dimethyl-p-phenylenediamine, N,N-diethyl-p-phenylenediamine, N-carbamidomethyl-N-methyl-p-phenylenediamine, N-carbamidomethyl-N-tetrahydrofurfuryl-2-methyl-p-phenylenediamine, N-ethyl-N-carboxymethyl-2-methyl-p-phenylenediamine, N-carbamidomethyl-N-ethyl-2-methyl-p-phenylenediamine, N-ethyl-N-tetrahydrofurfuryl-2-methyl-p-aminophenol, 3-acetylamino-4-aminodimethyl aniline, N-ethyl-N-β-methanesulfonamidoethyl-4-aminoaniline, N-ethyl-N-β-methanesulfonamidoethyl-3-methyl-4-aminoaniline, N-methyl-N-β-sulfoethyl-p-phenylenediamine, N-ethyl-N-p-methoxyethyl-3-methyl-4-aminoaniline, N-ethyl-N-[2-(2-methoxyethoxy)ethyl]-3-methyl-4-aminoaniline, N-ethyl-N-{2-[2-(2-methoxyethoxy)ethoxy]ethyl}-3-methyl-4-aminoaniline and N-ethyl-N-[[2-{2-((2-[2-(2-methoxyethoxy)-ethoxy]ethoxy))ethoxy}ethyl]]-3-methyl-4-aminoaniline with an inorganic acid such as a hydrochloric acid or a sulfuric acid or organic acid such as a p-toluenesulfonic acid.

It is also effective to treat the silver halide color photographic material containing the compound according to this invention with a color developing solution which contains both a primary aromatic amine color developing agent and an oxidizing agent which subjects the metal silver image to redox reaction.

On the application of such color developing solution, the color developing agent is oxidized by said oxidizing agent and then subjected to coupling with a color coupler for photograph to form a dye image. Such color developing solution is disclosed, for example, in Japanese Patent Laid-Open-to-Public No. 48-9729. A preferable oxidizing agent for this purpose is a cobalt complex having the coordination number of 6. The color photographic treatment using such color developing solution is particularly effective to the so-called silver-less color photographic material wherein the amount of silver is reduced than that in the ordinary silver halide color photographic material.

Particularly useful cobalt complexes contain a ligand selected from the group consisting of ethylene-diamine, ethylenetriamine, triethylenetetraamine, amine, nitrate, nitrite, azide, chloride, thiocyanate, isothiocyanate, water and carbonate and have (1) at least two ethylenediamine ligands, (2) at least five amine ligands or (3) at least one triethylenetetraamine ligand. Particularly preferable cobalt complexes are those shown by the following formulae:

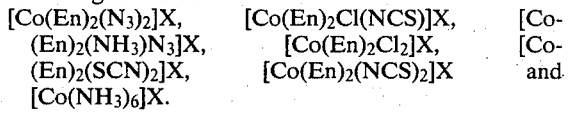

In the above formulae, En represents ethylene-diamine and X represents at least one anion selected from the group consisting of a chloride, bromide, nitrite, nitrate, perchlorate, acetate, carbonate, sulfite, sulfate, hydrochloride, thiocyanate, isothiocyanate and hydroxide. The most preferable complex is a hexaamine salt of cobalt, for example, chloride, bromide, sulfite, sulfate, perchlorate, nitrite and acetate. The cobalt complex to be used in the color developing solution is in general in the concentration range of about 0.1 to 50 g, more preferably about 1 g to about 15 g per liter of the color developing solution.

Furthermore, the silver halide color photographic material containing the compound according to the present invention can be treated also by such color photographic treatment that comprises developing said material in a color developing solution containing a primary aromatic amine color developing agent and then contacting the material with an amplifying solution which contains the oxidizing agent as above mentioned, for example, a cobalt complex having the coordination number of 6 in the presence of a principal color developing agent which is preferably received in the light-sensitive layer during the color developing step and moved into an amplifying bath. Another oxidizing agent preferable to this purpose is, for example, the aqueous hydrogen peroxide solution described in Japanese Patent Laid-Open-to-Public No. 51-16023. The amplifying solution may preferably contains a silver halide developing inhibitor in addition to the oxidizing agent and be used for the treatment of silver halide color photographic materials. According to this mode of practice, the amplification can be carried out under room lighting. According to this procedure, formation of dye can be observed and after accomplishment of the desired dye concentration, the amplification can be stopped. Preferable developing inhibitors include a water-soluble bromide compound such as potassium bromide, tetrazol free from a mercapto group or an ionic iodide group and a heterocyclic compound such as azaindene and triazole.

The concentration of a cobalt complex contained in the amplifying solution is in general about 0.2 g/l to about 20 g/l, most preferably about 1 to 15 g/l, and the concentration of the aqueous hydrogen peroxide solution is in general about 0.001–10%, most preferably about 0.5–5%. When a water-soluble bromide is used as the developing inhibitor, such bromide is contained in the amplifying solution in general in an amount of about 1 g/l to about 40 g/l. On the other hand, a developing inhibitor comprising a compound having a heterocyclic structure is usually used at the concentration of about 0.01 g/l to about 3 g/l. The amplifying bath is used in general at pH 6–14, preferably at pH 8–12.

The amplifying solution may contain, in addition to the above developing inhibitor, a developing accelerator, a stabilizing agent, a water-softening agent, a thickener, an unevenness inhibiting agent, etc.

The compounds according to this invention are satisfactorily effective also in the inhibition of fading of a diazo light sensitive material.

The present invention will be disclosed concretely in the following Examples but the embodiment of this invention should not be limited by these Examples.

EXAMPLE 1

45 g of exemplified cyan coupler (C-3), 200 mg of 2,5-di-tert.octylhydroquinone and 12 g of a fading inhibiting agent as specified herein later are dissolved in 22 g of dibutyl phthalate and 90 g of ethyl acetate. The solution is added to 500 ml of 5% aqueous gelatin solution containing sodium dodecylbenzenesulfonate and thereafter the solution is dispersed by means of a homogenizer. The resulting dispersion is added to 1000 ml of a red-sensitive silver chlorobromidee (containing 20 mole% of silver chloride) emulsion and, after the addition of 20 ml of 4% aqueous 2,4-dichloro-6-hydroxy-S-triazine sodium solution as a hardening agent, coated on a subbed polyester film and dried to give a light-sensitive silver halide photographic material.

In the above experiment, a sample in which the compound (1) is used as a fading inhibiting agent is defined as Sample I, a sample in which compound (2) is used as a fading inhibiting agent is defined as Sample II, a sample in which compound (29) is used as a fading inhibiting agent is defined as Sample III, a sample in which Tinuvin-P (trade name: obtainable from Ciba-Geigy) is used is defined as Comparative Sample A, a sample in which Tinuvin-PS (trade name: obtainable from Ciba-Geigy) is used is defined as Comparative Sample B and a sample quite free from any fading inhibitor is defined as blank. After being subjected to optical wedge exposure, these samples are treated according to the treatment procedures as disclosed hereinbefore and thereafter stored for 14 days in the dark at 70° C. and 80% RH (relative humidity) and for 7 days under approximately dry atmosphere at 77° C. Then, the remaining concentration of the cyan dye image at the initial density of 1.0 was determined. The results are shown in Table 1, in which Tinuvin-P and Tinuvin-PS are trade names for 2-(2'-hydroxy-5'-methylphenyl)benzotriazole and 2-(2'-hydroxy-5'-tert.butyl-phenyl)benzotriazole, respectively.

TABLE 1

| Sample | 70° C. 80% RH, for 14 days | 77° C. for 7 days |
|---|---|---|
| Blank | 0.83 | 0.72 |
| Comparative sample A | 0.86 | 0.75 |
| Comparative sample B | 0.88 | 0.77 |
| Sample I | 0.91 | 0.82 |
| Sample II | 0.97 | 0.85 |
| Sample III | 0.92 | 0.82 |

It is apparent from the above table that the compounds according to this invention exhibit excellent fading inhibiting effect.

EXAMPLE 2

An emulsion prepared in a similar manner as defined in Example 1 by using a cyan coupler, fading inhibiting agent and solvent as specified in Table 2-1 was coated on a polyethylene coated paper serving as the support to form a sample. The proportion of the quantity of silver to coupler, however, was adjusted so that the quantity of silver to a coupler having an active point substituent (couplers C-3 and C-5) may be half of that to a coupler having no substituent (couplers C-1 and C-9).

These samples were treated according to the following course of treating steps and then the remaining concentration of cyan dye image at the initial density of 1.0 was determined in a similar manner as defined in Example 1 to obtain results as shown in Table 2-2.

Treatment steps:
Color developing, 3.5 min.
Bleaching and fixing, 1.5 min.
Washing with water, 3.5 min.

In this experiment, the compositions of the color developing solution and the bleach-fixing solution are as defined herein before.

TABLE 2-1

| Sample No. | Type and Amount of Coupler | Type and Amount of Fading Inhibiting Agent | High-boiling Solvent | Low-boiling Solvent |
|---|---|---|---|---|
| 1 | Coupler C-3 45G | — | DBP 22g | EA 90g |
| 2 | " | Tinuvin 326 12g | " | " |
| 3 | " | Compound(3)12g | " | " |
| 4 | " | Compound(11)12g | " | " |
| 5 | Coupler C-9 50g | — | TPP 23g | MA 90g |
| 6 | " | Tinuvin 327 12g | " | " |
| 7 | " | Compound(2)12g | " | " |
| 8 | " | Compound(5) 6g Compound(6) 6g | " | " |
| 9 | Coupler C-1 45g | — | DBP 22g | EA 90g |
| 10 | " | Tinuvin 326 12g | " | " |
| 11 | " | Compound(2) 6g Compound(4) 6g | " | " |
| 12 | " | Compound(30)12g | " | " |
| 13 | Coupler C-5 57g | — | DBP 11g TCP 11g | EA 90g EA 90g |
| 14 | " | Tinuvin 327 12g | " | " |
| 15 | " | Compound(14)12g | " | " |
| 16 | " | Compound(46)12g | " | " |

In the Table, DBP represents dibutyl phthalate, TCP represents tricresyl phosphate, TPP represents triphenyl phosphate, EA represents ethyl acetate and MA represents methyl acetate. Further, Tinuvin 326 and Tinuvin 327 are trade names for 2-(2'-hydroxy-3'-tert.-butyl-5'-methylphenyl)-5-chlorobenzotriazole and 2-(2'-hydroxy-3',5'-di-tert.butyl-phenyl)-5-chlorobenzotriazole, respectively.

TABLE 2-2

| Sample No. | 70° C., 80% RH, for 14 days | 77° C., for 7 days |
|---|---|---|
| 1 | 0.67 | 0.52 |
| 2 | 0.79 | 0.70 |
| 3 | 0.93 | 0.84 |
| 4 | 0.92 | 0.82 |
| 5 | 0.85 | 0.76 |
| 6 | 0.90 | 0.85 |
| 7 | 0.95 | 0.90 |
| 8 | 0.94 | 0.89 |
| 9 | 0.83 | 0.75 |
| 10 | 0.87 | 0.84 |
| 11 | 0.96 | 0.91 |
| 12 | 0.95 | 0.92 |
| 13 | 0.82 | 0.75 |
| 14 | 0.87 | 0.85 |
| 15 | 0.95 | 0.93 |
| 16 | 0.92 | 0.90 |

As apparent from the above, the compounds according to this invention exhibit excellent fading inhibiting effect on various couplers. Furthermore, two or more of the present compounds may be used in combination. Such combination was convenient for dispersing, because combined compounds of this invention increase solubility in a solvent.

EXAMPLE 3

Example 2 was repeated except for use of a composition comprising a coupler having the composition as defined in Table 3-1, fading inhibiting agent and solvent to form a sample. After the optical wedge exposure samples were treated in a similar manner as in Example 2 and then the remaining concentrations of the cyan dye at 1.0 of initial density were defined. The results obtained will be shown in Table 3-2.

TABLE 3-1

| Sample No. | Type and Amount of Coupler | Fading Inhibiting Agent | High-boiling Solvent | Low-boiling Solvent |
|---|---|---|---|---|
| 17 | Coupler C-1 46g | — | DBP 22g | EA 90g |
| 18 | " | Tinuvin 320 12g | " | " |
| 19 | " | Present compound(4) 12g | " | " |
| 20 | " | Tinuvin 320 6g Present compound(4) 6g | " | " |

Tinuvin 320 is the trade name for 2-(2'-hydroxy-3',5'-di-tert.butyl-phenyl)benzotriazole.

TABLE 3-2

| Sample No. | 70° C., 80% RH, for 14 days | 77° C., for 7 days |
|---|---|---|
| 17 | 0.82 | 0.74 |
| 18 | 0.88 | 0.81 |
| 19 | 0.96 | 0.93 |
| 20 | 0.94 | 0.90 |

As shown by the above results, no adverse effect is caused by the combination of 2-(2'-hydroxyphenyl)benzotriazole and the present compound. Thus, it is possible to use these compounds in combination.

EXAMPLE 4

On the polyethylene coated paper, each of the following layers was coated successively from the side of a support to form a silver halide color photographic material (Sample 1):

First layer

Blue-sensitive silver halide emulsion layer which comprises a silver chlorobromide emulsion containing 10 mol% of silver chloride. This emulsion contains 400 g of gelatin per mol of silver chloride, is sensitized with $2.5 \times 10^{-4}$ mol per mol of silver halide of the sensitizing dye of the structural formula

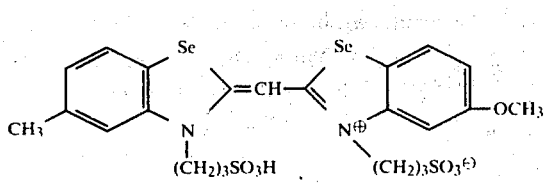

and further contains per mol of silver halide $2 \times 10^{-1}$ mol of the yellow coupler which has been dissolved and dispersed in dibutyl phthalate, said coupler being α-[4-(1-benzyl-2-phenyl-3,5-dioxo-1,2,4-triazolyginyl)]-α-pivalyl-2-chloro-5-[γ-(2,4-di-tert.amyl-phenoxy)-butylamido]acetanilide. The emulsion is coated in such amount that the amount of silver is 400 mg/m².

Second layer

Gelatine layer. This layer is coated so that the thickness of dry film is 1μ.

Third layer

Green-sensitive silver halide emulsion layer which comprises a silver chlorobromide emulsion containing 40 mol% of silver chloride. Said emulsion contains 500 g of gelatin per mol of silver halide, is sensitized with $2.5 \times 10^{-4}$ mol per mol of silver halide of the sensitizing dye of the structural formula

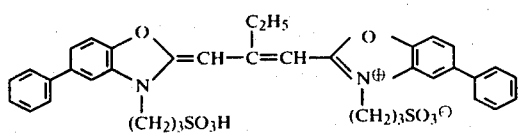

and further contains $2 \times 10^{-1}$ mol per mol of silver halide of the magenta coupler, that is 4,4'-benzilidene bis[1-(2,3,4,5,6-pentachlorophenyl)-3-{2-chloro-5-[γ-(2,4-di-tert.amyl-phenoxy)butylamido]anilino}5-pyrazelone] which has been dissolved and dispersed in tricresyl phosphate and 30 W% of 2,2,7- and 2,2,5- and 2,2,8-trimethyl-6-octyloxychromane mixture per coupler. This layer is coated in such amount that the amount of silver is 500 mg/m².

Fourth layer

This layer is coated so that a gelatin layer of the thickness of 1μ in which 30 mg/m² of di-tert.-octylhydroquinone and 0.7 g/m² of 2-(2'-hydroxy-3'-sec.butyl-5'-tert.butylphenyl)benzotriazole which have been dissolved in dibutyl phthalate are contained is formed.

Fifth layer

Red-sensitive silver halide emulsion layer which comprises a silver chlorobromide emulsion containing 20 mol% of silver chloride. This layer contains 500 g of gelatin per mol of silver halide, is sensitized with $2.5 \times 10^{-4}$ mol per mol of silver halide of the sensitizing dye of the structural formula

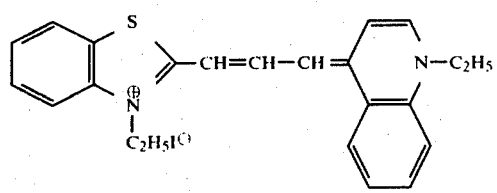

and further contains $2 \times 10^{-1}$ mol per mol of silver halide of cyan coupler (C-3) which has been dissolved and dispersed in tricresyl phosphate. This layer is coated in such amount that the amount of silver is 500 mg/m².

Sixth layer

Protective layer (which comprises gelatin layer and is coated so that the thickness of dry film is 1μ.)

The silver halide emulsion used in each of the above light-sensitive layers (the first, third and fifth layers) is prepared by the method described in Japanese Patent Publication No. 46-7772, chemically sensitized with sodium thiosulfate 5 hydrate and incorporated with 4-hydroxy-6-methyl-1,3,3a,7-tertraindene as the stabilizer, bis(vinylsulfonylmethyl)ether as a hardening agent and saponin as the coating aid.

Then, a coupler to which Tinuvin-327 has been added in the amount of 30% by weight based on the coupler is added dispersedly to the fifth layer to give Sample 2. Similarly, compound (4) of the present invention is added dispersedly to the fifth layer in the same manner as in Sample 2 to give Sample 3.

These samples are exposed through optical wedges to blue light, green light and red light, respectively and treated in the same manner as in Example 2. The dye concentration of each sample was determined after the storage for 7 days in the dark at 70° C. and 80% RH and after storage for 7 days under approximately dry atmosphere at 77° C. The results obtained are shown in Table 4-1.

TABLE 4-1

| Sample No. | 70° C., 80% RH, for 7 days | | | 77° C. for 7 days | | |
|---|---|---|---|---|---|---|
| | Yellow | Magenta | Cyan | Yellow | Magenta | Cyan |
| 21 | 0.97 | 0.98 | 0.68 | 0.85 | 0.87 | 0.48 |
| 22 | 0.98 | 0.98 | 0.80 | 0.85 | 0.86 | 0.71 |
| 23 | 0.98 | 0.99 | 0.93 | 0.85 | 0.86 | 0.82 |

It will be noted from the above results that the compound according to this invention is actually effective against fading inhibition of a cyan dye image.

What we claim is:

1. A silver halide color photographic material comprising a support and a silver halide light-sensitive layer containing a phenol or naphthol cyan coupler and a 2-phenyl benzotriazole compound having in the 2'-position an —OR group wherein R is an organic residue wherein said 2-phenyl benzotriazole compound is represented by the formula:

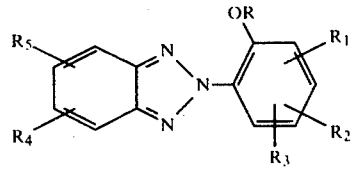

wherein R represents an alkyl, alkenyl, cycloalkyl, aryl, aralkyl, acyl, alkylsulfonyl, or arylsulfonyl group, an N-substituted carbamoyl or sulfamoyl group, or a oxalyl, oxamoyl, oxycarbonyl or oxaacetyl group having an alkyl, aryl or aryloxy group; $R_1$, $R_2$, $R_3$, $R_4$ and $R_5$ each represent hydrogen, halogen, an alkyl, alkenyl, aryl, aralkyl, alkoxy, aryloxy, acyloxy, alkylthio, arylthio, monoalkylamino, dialkylamino, acylamino, sulfonamido, or nitro group, the residue of a sulfonic acid or the ester or salt thereof, the residue of a carboxylic acid or the ester or salt thereof; and $R_4$ and $R_5$ can cooperatively form a 5- or 6-membered carbocyclic ring.

2. The color photographic material according to claim 1 wherein the photographic material further comprises 2,5-di-octyl-hydroquinone, 2,5-di-tert.amyl-hydroquinone or 2,5-di-tert.butyl-hydroquinone.

* * * * *